United States Patent [19]

Dent

[11] 4,392,859
[45] Jul. 12, 1983

[54] FITMENTS FOR INJECTION DEVICES

[75] Inventor: Hugh R. Dent, Malmesbury, England

[73] Assignee: Sterimatic Holdings Limited, Tortola, British Virgin Isls.

[21] Appl. No.: 287,775

[22] Filed: Jul. 28, 1981

[30] Foreign Application Priority Data

Jul. 29, 1980 [GB] United Kingdom ............... 8024765
Sep. 25, 1980 [GB] United Kingdom ............... 8030985

[51] Int. Cl.³ ............................................. A61M 5/00
[52] U.S. Cl. .................................... 604/198; 604/263
[58] Field of Search ............ 128/218 R, 218 F, 218 S, 128/215, 220, 221, 224

[56] References Cited

U.S. PATENT DOCUMENTS 1,921,034  8/1933  La Marche ................. 128/218 F
3,134,380  5/1964  Armao ........................ 128/215
3,354,881 11/1967  Bloch ......................... 128/215

Primary Examiner—John D. Yasko
Attorney, Agent, or Firm—Young & Thompson

[57] ABSTRACT

In order to minimize the risk of infection when a large number of animals are injected with the same needle, the injecting gun is provided with a stainless steel sleeve which surrounds the needle. The sleeve comprises a first tube attached to the needle connecting body and a second tube telescopically slidable within the first tube against a spring. A detachable plastics cap incorporating a sterilizing substance is fitted on the free end of the second tube. In use of the gun to inject an animal, the cap is applied to the proposed site of injection and pressure is applied to the gun to cause the tubes to telescope, so that the point of the needle passes through the sterilizing substance and punctures the skin of the animal. On releasing the applied pressure, the point of the needle will be withdrawn from the animal and will pass back through the sterilizing substance under the action of the spring.

17 Claims, 2 Drawing Figures

FITMENTS FOR INJECTION DEVICES

BACKGROUND OF THE INVENTION

This invention relates to fitments for injection devices of the kind in which injection liquid is delivered though a hollow needle. Such devices are used for injecting humans, animals, trees, fruit or vegetables, for example.

Farmers have for many years given routine oral drenches of anthelminthics to suppress the effects of intestinal and other parasitic worms in cattle, sheep and pigs. However these drenches only become effective after a relatively long period. Although it has recently become possible to achieve the same effect in a much shorter space of time by injecting the animal, there has been a reluctance by farmers to use the new method. This is because it is not usual to sterilize the site of injection either before or after injection. Moreover the same needle is often used for injecting a large number of animals without sterilizing the needle between each injection, in view of the large number of animals which have to be injected at one time, so that the site of injection often becomes infected leading to an abscess. Also, especially with sheep, there are several routine injections given to stop various clostridial complications, and each time the animal is injected it increases the risk of rejection of the carcass for human consumption due to abscesses. It is an object of this invention to provide injection devices of the kind referred to with fitments which enable the devices to be used by farmers to inject a large number of animals in a short space of time whilst minimising any subsequent injection at the site of injection.

SUMMARY OF THE INVENTION

According to the invention there is provided a fitment for attachment to an injection device of the kind in which injection liquid is delivered through a hollow needle, the fitment comprising means for sterilizing the needle prior to application of the needle to the site of injection.

Whilst the word "sterilizing" is used in this specification in the sense of killing micro-organisms, such as bacteria or viruses, it should be understood that it is not essential that all micro-organisms are killed, that is to say that the needle is rendered absolutely sterile. The sterilizing means may, for example, comprise a sterilizing substance in the form of a liquid, gel or powder.

Since the needle is sterilized before it punctures the skin, there is little chance of the wound being infected by the needle, even if the same needle is used for performing a number of injections. Furthermore, where the sterilizing means comprise a sterilizing substance, some of the sterilizing substance coating the needle may be transferred to the site of the injection.

The sterilizing means are preferably so disposed on the fitment that, when the fitment is attached to an injection device, at least a leading portion of the needle is movable through the sterilizing means prior to application of the needle to the site of injection. This enables the needle to be sterilized and the injection to be effected in a single movement, so that a large number of injections may be carried out in a short space of time.

In a preferred embodiment of the invention the fitment comprises a first part for attachment to the injection device and a second part connected to the first part so as to be reciprocable relatively thereto in the direction of the length of the needle, the sterilizing means being carried on the second part and lying on the longitudinal axis of the needle, when the fitment is attached to an injection device, whereby said relative movement between the two parts of the fitment effects said movement of the needle through the sterilizing means. Spring means are conveniently provided to bias the relatively movable parts away from one another. In use the second part is simply placed against the site of injection and the first part is moved relative to the second part so as to cause the needle to pass through the sterilizing means into the injection site.

The sterilizing means may comprise a holder for locting a sterilizing substance within the fitment, the sterilizing substance possibly being impregnated in a body of absorbent material. The holder is preferably detachable from the fitment so that it may be replaced by a new holder incorporating fresh sterilizing substance when desired.

In one form of the invention the sterilizing means comprise a radioactive substance so disposed as to provide within the fitment a radioactive sterilizing field through which, when the fitment is attached to an injection device, at least a leading portion of the needle is movable prior to application of the needle to the site of injection.

In another form of the invention the sterilizing means comprise a reservoir for a sterilizing fluid in communication with a nozzle for injecting the fluid into a chamber which, when the fitment is attached to an injection device, surrounds at least a leading portion of the needle whereby said portion of the needle may be coated with said fluid prior to application of the needle to the site of injection.

The invention also provides an injection device comprising a support for a hollow needle, a reservoir for injection liquid, means for delivering injection liquid from the reservoir through the needle, and a fitment including means for sterilizing the needle prior to application of the needle to the site of injection.

BRIEF DESCRIPTION OF THE DRAWINGS

In order that the invention may be more fully understood, an embodiment of the invention will now be described, by way of example, with reference to the accompanying drawing, in which.

DETAILED DESCRIPTION OF THE DRAWINGS

Figures 1, 2:
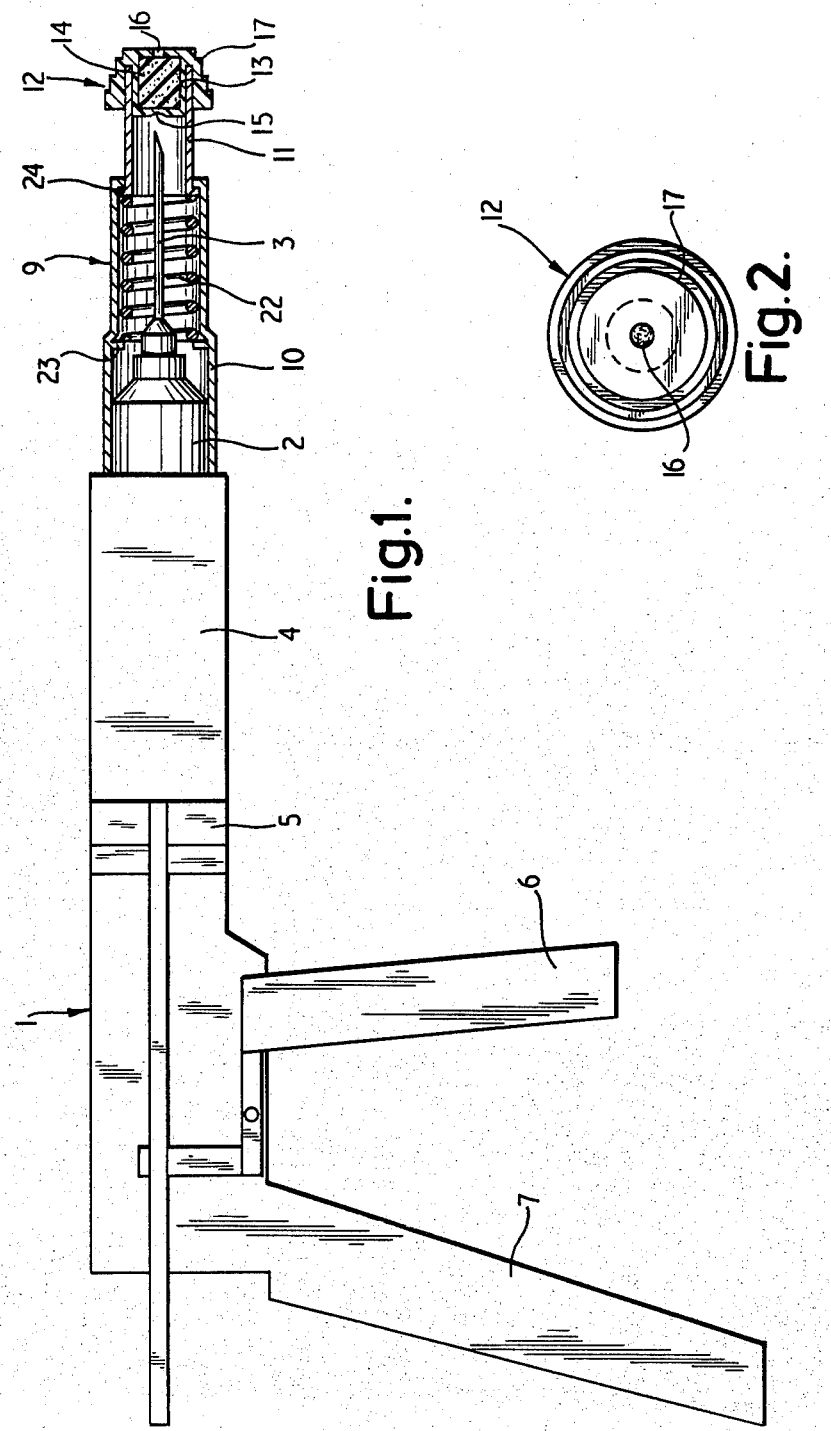
FIG. 1 is a schematic diagram of an injection device incorporating a fitment which is shown in section.
FIG. 2 is an end view of the fitment.

The illustrated device comprises an injecting gun 1 of the type used for injecting cattle, sheep or pigs. The gun 1 includes a needle connecting body 2, a hollow metal needle 3, a reservoir 4 for injection liquid, a piston 5, an actuating lever 6 for displacing the piston 5 to supply injection liquid to the needle 3, and a handle 7. A stainless steel sleeve 9 is a push fit on the needle connecting body 2, a slot (not shown) optionally being provided in the end of the sleeve 9 to enable the end of the sleeve to expand slightly to accommodate the connecting body 2.

The sleeve 9 comprises a first tube 10 attached to the needle connecting body 2, and a second tube 11 telescopically slidable within the first tube 10. The second tube 11 is biased into its extended position by a return spring 22 within the first tube 10 between an annular flange 23 on the first tube 10 and an annular flange 24 on the second tube 11.

A detachable plastics cap 12 incorporating an enclosure 13 for a sterilizing substance is an interference fit on the free end of the second tube 11. The enclosure 13 contains a sponge 14 impregnated with a sterilizing gel. Furthermore the enclosure 13 incorporates a weakened portion 15 and an aperture 16 lying on the longitudinal axis of the needle 3. The cap 12 is provided with step formations 17 on its outer surface in order to make it easier to remove the cap 12 from the end of the second tube 11. If desired, a reservoir for sterilizing substance may be clipped to the top of the gun 1, and sterilizing substance may be supplied to the cap 12 from this reservoir by means of a feed tube.

In use of the gun 1 to inject an animal, it is first ensured that the cylinder 4 contains a quantity of injection liquid and that a sterilizing cap 12 is fitted to the free end of the second tube 11. The end of the cap 12 is then applied to the proposed site of injection on the animal, and pressure is applied to the gun so as to cause the tubes 10, 11 to telescope so that the point of the needle 3 passes through the enclosure 13 and punctures the skin of the animal. More particularly the point of the needle 3 punctures the weakened portion 15 of the enclosure 13, moves through the impregnated sponge 14 and then passes through the aperture 16 in the end wall of the enclosure 13. The needle 3 is thereby cleaned and coated with a layer of the sterilizing gel prior to its penetrating the skin. The action of the needle puncturing the skin may serve to transfer sterilizing substance to the skin thereby sterilizing the site of the injection. When the needle 3 has been pushed through the skin to the required depth the lever 6 is operated to administer the required dose of injection liquid. Optionally the second tube 11 is guided within the first tube 10 by guides (not shown) which are slightly skew with respect to the longitudinal axis of the first tube 10 so that the tube 11 rotates through a small angle as the tubes are telescoped, thereby providing a scrubbing action on the needle 3 by the sponge 14.

As the needle 3 is withdrawn, the second tube 11 is caused to return to its extended position by the return spring 22 so that the point of the needle 3 passes back through the sponge 14, thereby again cleaning the needle 3 and coating it with a layer of sterilizing gel. The injection has then been completed and the gun 1 may be moved away from the skin of the animal. The gun 1 can then be used for performing a second injection without any further adjustment having to be made. A large number of injections may be made using the same needle 3 and the same sterilizing cap 12 without appreciably increasing the risk of infection.

In a modification of the above-described embodiment of the invention, the arrangement is such that the position of the enclosure 13 is adjusted relative to the needle 3 between each injection so that, on performing a second injection, the point of the needle 3 will pass through a different region of the sponge 14 to that through which it passed on performing the first injection. For example, the arrangement may be such that the enclosure 13 is rotatable and the point of the needle passes through the enclosure 13 along a path parallel to, but offset from, the axis of rotation of the enclosure 13. After the first injection has been carried out, the enclosure 13 may be rotated about its axis through a limited angle prior to the second injection being performed, this rotation possibly being performed by indexing means coupling the second tube 11 to the first tube 10 and actuated by telescoping of the tubes.

Instead of providing a sponge 14 impregnated with sterilizing substance through which the point of the needle 3 passes in use, a spray nozzle may be provided in a wall of the sleeve 9 for spraying the needle with a sterilizing liquid or powder when a valve is actuated by telescoping of the tubes 10 and 11. As a further alternative a sterilizing cap may be provided containing a radioactive substance which provides a radioactive sterilizing field through which the point of the needle 3 moves prior to an injection. The radioactive substance may be in the form of a radioactive coating on the internal walls of the cap, and screening is provided by means of lead.

In the embodiment illustrated the sleeve 9 is detachable from the gun 1 to enable a new needle 3 to be fitted to the gun 1. However it is also possible for the sleeve to be integrally formed with the remainder of the injection device, more particularly where the injection device is a disposable plastics syringe of the type used for injecting humans. In this case the sterilizing substance may be impregnated in a sponge provided at the end of a collapsible plastics sleeve surrounding the needle and comprising a flexible intermediate portion provided with slots extending substantially parallel to the axis thereof. On performing an injection, the flexible intermediate portion will bow outwardly enabling the point of the needle to move through the sponge prior to puncturing the skin.

What I claim is:

1. A sterilizing fitment for an injection device of the kind in which injection liquid is delivered through a hollow needle, the fitment being provided to sterilize the needle prior to its application to the site of injection and again on withdrawal of the needle from the site of injection, which fitment comprises a collapsible sleeve comprising two telescoping tubes for surrounding the needle, means at one end of the sleeve on one of said tubes for attaching the sleeve to a needle support of the injection device, wall means at the other end of the sleeve on the other of said tubes closing off said other end so as to enclose the needle, and sterilizing means in the vicinity of said other end of the sleeve, the two ends of the collapsible sleeve being reciprocable relative to one another in the direction of the length of the needle and being resiliently biased in the extended position, whereby, in use, when an injection is effected by placing said other end of the sleeve against the injection site and applying pressure to the injection device in a direction towards the injection site, the point of the needle moves through the wall means and the sterilizing means into the injection site as the sleeve collapses under the applied pressure and subsequently moves back through the wall means and the sterilizing means as the sleeve reassumes its extended position on release of said pressure.

2. A fitment according to claim 1, wherein the sterilising means comprise a holder for locating a sterilising substance within the fitment.

3. A fitment according to claim 2, wherein the holder holds a body of absorbent material for impregnation with a sterilising substance.

4. A fitment according to claim 2, wherein the holder is detachable from the fitment.

5. A fitment according to claim 1, wherein the sterilising means comprise a radioactive substance so disposed as to provide within the fitment a radioactive sterilising field through which, when the fitment is attached to an injection device, at least a leading portion of the needle is movable prior to application of the needle to the site of injection.

6. A fitment according to claim 1, wherein the sterilising means comprise a reservoir for a sterilising fluid in communication with a nozzle for injecting the fluid into a chamber which, when the fitment is attached to an injection device, surrounds at least a leading portion of the needle whereby said portion of the needle may be coated with said fluid prior to application of the needle to the site of injection.

7. A fitment according to claim 1, wherein the two tubes are biased into the extended position by means of a spring within the sleeve.

8. An injection device comprising a support for a hollow needle, a reservoir for injection liquid, means for delivering injection liquid from the reservoir through the needle, and a fitment for sterilizing the needle prior to application of the needle to the site of injection and again on withdrawal of the needle from the site of injection, the fitment comprising a collapsible sleeve comprising two telescoping tubes for surrounding the needle, one end of the sleeve being attached by one of said tubes to the needle support, wall means at the other end of the sleeve on the other of said tubes closing off said other end so as to enclose the needle, and sterilizing means in the vicinity of said other end of the sleeve, the two ends of the collapsible sleeve being reciprocable relative to one another in the direction of the length of the needle and being resiliently biased in the extended position, whereby, when an injection is effected by placing said other end of the sleeve against the injection site and applying pressure to the injection device in a direction towards the injection site, the point of the needle moves through the wall means and the sterilizing means into the injection site as the sleeve collapses under the applied pressure and subsequently moves back through the wall means and the sterilizing means as the sleeve reassumes its extended position on release of said pressure.

9. An injection device according to claim 8, wherein the sterilising means comprise a holder for locating a sterilising substance within the fitment.

10. An injection device according to claim 9, wherein the holder holds a body of absorbent material for impregnation with a sterilising substance.

11. An injection device according to claim 9, wherein the holder is detachable from the fitment.

12. An injection device according to claim 8, wherein the sterilising means comprise a radioactive substance so disposed as to provide within the fitment a radioactive sterilising field through which at least a leading portion of a needle attached to said support is movable prior to application of the needle to the site of injection.

13. An injection device according to claim 8, wherein the sterilising means comprise a reservoir for a sterilising fluid in communication with a nozzle for injecting the fluid into a chamber which surrounds at least a leading portion of a needle attached to the support whereby said portion of the needle may be coated with said fluid prior to application of the needle to the site of injection.

14. A sterilising substance holder for use in the fitment according to claim 4, or in the injection device according to claim 11, comprising an enclosure containing a sterilising substance, and means for detachably connecting the enclosure to the fitment.

15. A sterilising substance holder according to claim 14, wherein the enclosure contains a body of absorbent material impregnated with the sterilising substance.

16. A fitment according to claim 8, wherein the two tubes are biased into the extended position by means of a spring within the sleeve.

17. A sterilizing substance holder for a sterilizing fitment for an injection device of the kind in which injection liquid is delivered through a hollow needle, the fitment being provided to sterilize the needle prior to its application to the site of injection and against on withdrawal of the needle from the site of injection and comprising a collapsible sleeve comprising two telescoping tubes for surrounding the needle and attachable at one end of said sleeve by one of said tubes to a needle support of the injection device, the two ends of the collapsible sleeve being reciprocable relative to one another in the direction of the length of the needle and being resiliently biased in the extended position, the holder being adapted to be fitted to the other end of the sleeve on the other of said tubes to close off said other end so as to enclose the needle and comprising an enclosure containing a body of absorbent material impregnated with a sterilizing substance, whereby, in use, when an injection is effected by placing said other end of the sleeve with the holder fitted thereto against the injection site and applying pressure to the injection device in a direction towards the injection site, the point of the needle moves through the enclosure into the injection site as the sleeve collapses under the applied pressure and subsequently moves back through the enclosure as the sleeve reassumes its extended position on release of said pressure.

* * * * *